(12) United States Patent
Richardson et al.

(10) Patent No.: US 12,270,573 B2
(45) Date of Patent: Apr. 8, 2025

(54) AEOLIAN ANTI-VIRAL ULTRA-VIOLET SYSTEM FOR FLUIDIC PURIFICATION

(71) Applicants: Donald S. Richardson, Providence, RI (US); Nicholas Richardson, Providence, RI (US)

(72) Inventors: Donald S. Richardson, Providence, RI (US); Nicholas Richardson, Providence, RI (US)

( * ) Notice: Subject to any disclaimer, the term of this patent is extended or adjusted under 35 U.S.C. 154(b) by 746 days.

(21) Appl. No.: 17/472,520

(22) Filed: Sep. 10, 2021

(65) Prior Publication Data

US 2022/0074615 A1     Mar. 10, 2022

Related U.S. Application Data

(60) Provisional application No. 63/076,545, filed on Sep. 10, 2020.

(51) Int. Cl.
    *F24F 8/22*     (2021.01)
    *A61L 9/20*     (2006.01)

(52) U.S. Cl.
    CPC ............ *F24F 8/22* (2021.01); *A61L 9/20* (2013.01); *A61L 2209/12* (2013.01); *A61L 2209/15* (2013.01)

(58) Field of Classification Search
None
See application file for complete search history.

(56) References Cited

U.S. PATENT DOCUMENTS

| | | | |
|---|---|---|---|
| 3,804,942 A | 4/1974 | Kato et al. | |
| 4,011,456 A * | 3/1977 | Bredewater | B01J 19/123 250/492.1 |
| 5,523,057 A | 6/1996 | Mazzilli | |
| 6,022,511 A * | 2/2000 | Matschke | A61L 9/20 250/436 |
| 6,063,170 A | 5/2000 | Deibert | |
| 6,623,544 B1 | 9/2003 | Kaura | |
| 6,849,107 B1 | 2/2005 | Huffman | |

(Continued)

FOREIGN PATENT DOCUMENTS

| | | |
|---|---|---|
| ES | 2169007 A1 | 6/2002 |
| GB | 2036951 A | 7/1980 |

(Continued)

*Primary Examiner* — Andrew Smyth
(74) *Attorney, Agent, or Firm* — Thomas P. O'Connell; O'Connell Law Firm (57) ABSTRACT

A fluid purification system for purifying a fluid, such as air, within a fluid flow system, such as a heating, ventilation, and air conditioning system. The fluid purification system has a housing with a specular interior surface. An aerodynamic ultra-violet light module is retained by a framework within the housing to be surrounded by the specular interior surface. The light module has an aerodynamic intake nose cone adjacent to the first end of the housing and an aerodynamic exhaust tail cone adjacent to the second end of the housing. The nose and tail cones are eye-shaped, taper distally, and cooperate to retain a plurality of ultra-violet bulbs in an eye-shaped array that communicates longitudinally within the housing. The housing can be rectangular in cross section with upper and lower walls and opposed sidewalls. Each wall can have a concave inwardly-facing surface operative to focus ultra-violet light within the housing.

15 Claims, 8 Drawing Sheets

(56) References Cited

U.S. PATENT DOCUMENTS

| | | |
|---|---|---|
| 7,824,626 B2 | 11/2010 | Kwiatkowski |
| 8,845,782 B2 | 9/2014 | Metteer |
| 9,597,627 B2 | 3/2017 | Zhang |
| 10,226,546 B2 | 3/2019 | Leonaggeo |
| 10,451,298 B2 | 10/2019 | Matschke et al. |
| 10,702,623 B2 | 7/2020 | Carbone et al. |
| 2002/0144601 A1 | 10/2002 | Palestro et al. |
| 2003/0021721 A1* | 1/2003 | Hall .................. A61L 9/16 422/4 |
| 2005/0150386 A1* | 7/2005 | Cheng ................ B01D 46/521 96/226 |
| 2006/0196360 A1 | 9/2006 | Hecker et al. |
| 2007/0227362 A1* | 10/2007 | Parker ............... B01D 46/0028 96/224 |
| 2008/0053311 A1 | 3/2008 | Lee |
| 2009/0049985 A1 | 2/2009 | Leroux et al. |
| 2010/0172793 A1 | 7/2010 | Obee et al. |
| 2013/0248734 A1 | 9/2013 | Berry |

FOREIGN PATENT DOCUMENTS

| | | | |
|---|---|---|---|
| GB | 2418335 A | 3/2006 | |
| WO | WO-2011140964 A1 * | 11/2011 | ............. A61L 9/014 |
| WO | WO2014181008 A1 | 11/2014 | |
| WO | WO-2020243087 A1 * | 12/2020 | ............... A61L 2/10 |

* cited by examiner

AEOLIAN ANTI-VIRAL ULTRA-VIOLET SYSTEM FOR FLUIDIC PURIFICATION

RELATED APPLICATION

This application claims priority to Provisional Application No. 63/076,545, filed Sep. 10, 2020, the entirety of which being incorporated herein by reference.

FIELD OF THE INVENTION

The present invention relates generally to the purification of fluids, including air. More particularly, disclosed herein is an Aeolian device for the purification of air and other fluids by the application of ultra-violet light.

BACKGROUND OF THE INVENTION

As has been demonstrated by the COVID-19 pandemic, viruses and other pathogens are capable of transmission not only through direct physical contact but also through the air. Accordingly, the suspension of air-transmissible viruses in the heating, ventilation, and air conditioning (HVAC) systems of building structures, including hospitals and nursing homes, is of enormous concern. The potential transmission of disease through the systems at the very core of building ventilation, heating, cooling, and air conditioning has a direct negative impact on fruitful building occupancy, and the resulting fear of such transmission has a huge negative impact on the physical and mental health of the public and the national economy.

Ultra-violet (UV) light has long been used to purify air and other fluids. Ultra-violet light has been applied, for instance, in complex purification systems installed within large buildings and in relatively simple, portable floor-supported devices. Indeed, such portable devices are plentiful in the commercial market. It is known to interpose ultra-violet air purification devices within ducted HVAC systems in an effort to purify the air passing through the ducts by the application of ultra-violet light.

Unfortunately, the ultra-violet air purification systems of the prior art have typically been interposed in a manner that substantially disrupts the smooth and natural airflow within the ducted system. Potential disruption to air flow can lead to poor system performance, energy losses, and other deleterious effects, which can discourage the implementation of such systems in the first instance.

The present inventors have thus appreciated that it would be advantageous to provide a system capable of purifying air and potentially other fluids within a fluidic flow system, such as but not limited air flowing through an HVAC system, by the application of ultra-violet light that minimizes disruption to natural fluidic flow.

SUMMARY OF THE INVENTION

With a recognition of the state of the art, the present invention is founded on the basic object of providing a system, which can be referred to as an Aeolian fluid purification system, for the purification of air within a ducted system by the application of ultra-violet light that represents minimal disruption to the flow of air through the ducted system.

A related object of embodiments of the invention is to provide a system for the purification of air within a ducted system that can not only be employed relative to newly-constructed HVAC systems but that can also be readily retrofitted to existing HVAC systems to purify building air in an efficient and effective manner.

A further object of manifestations of the invention is to provide a fluid purification system that can be implemented and accepted as a relatively low-cost and highly effective approach to eliminate viruses, such as the COVID-19 virus and its variants and other viruses, from the supply and/or return air of HVAC systems on a universal basis.

A further object of embodiments of the invention is to provide such a fluid purification system under which fabrication and installation can be carried out in an efficient and cost-effective manner and where distribution can be carried out on a national or worldwide basis thereby providing reassurance of virus-free building structures to a concerned public directly and quickly.

These and further objects, advantages, and details of the present invention will become obvious not only to one who reviews the present specification and drawings but also to those who have an opportunity to observe an embodiment of the Aeolian fluid purification system in operation. However, it will be appreciated that, although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In accomplishing one or more of the foregoing objects, an embodiment of the fluid purification system for purifying a fluid within a fluid flow system has a housing with a first end open to fluid entering the housing, a second end open to fluid exhausted from the housing, and a specular interior surface. A framework is fixed to the housing, and an aerodynamic ultra-violet light module is retained by the framework within the housing and is surrounded by the specular interior surface.

In practices of the invention, the ultra-violet light module has a first aerodynamic end cone comprising an intake nose cone disposed adjacent to the first end of the housing and a second aerodynamic end cone comprising an exhaust tail cone disposed adjacent to the second end of the housing. The intake nose cone and the exhaust tail cone cooperate to retain a plurality of ultra-violet bulbs in an array communicating longitudinally within the housing.

Under such constructions, the fluid purification system can be installed within a fluid flow system, such as a heating, ventilation, and air-conditioning system, with the first end adapted to receive fluid flow and the second end adapted to exhaust fluid flow after purification by application of ultra-violet light by the ultra-violet light module. For instance, the housing can be interposed between first and second spaced duct sections within a heating, ventilation, and air-conditioning system. With the housing and the fluid purification system so disposed, fluid entering the fluid purification system will enter the first end of the housing to pass over the intake nose cone, then over the ultra-violet light bulbs, and then over the exhaust tail cone before being exhausted through the second end of the housing.

The ultra-violet light bulbs and the ultra-violet light module can be electrically powered and can be actuated in any appropriate manner. Electrical power can thus be provided to the ultra-violet light module and the fluid purification system in general by any viable source of electrical power, including building power, battery power, generator power, or any other source of combination of sources. The ultra-violet light module can be continuously powered, powered only during active fluid flow through the system, selectively powered by manual actuation, or automatically powered intermittently or in response to a detected pathogen. The system could further incorporate a detection subsystem for detecting the presence of pathogens and triggering actuation of the ultra-violet light module in response thereto.

In certain embodiments of the fluid purification system, the first and second aerodynamic end cones of the ultra-violet light module have tapered distal portions. In such manifestations of the invention, the intake nose cone thus tapers toward the first end of the housing, and the exhaust tail cone tapers toward the second end of the housing. Still more particularly, the ultra-violet light module can have a symmetrical eye-shaped cross section, and the array of ultra-violet light bulbs can have an upper array of bulbs disposed along an upper arcuate path and a lower array of bulbs disposed along a lower arcuate path.

The highly-reflective, specular interior surface or surfaces can be formed in any effective way within the scope of the invention. In one non-limiting embodiment, the reflective surface is formed by a reflective polyester film, but polishing, mirrors, and numerous other effective mechanisms for creating a reflective surface will be obvious to one of skill in the art.

According to non-limiting embodiments disclosed herein, the housing can be rectangular in lateral cross section with an upper wall, a lower wall, and opposed sidewalls. Each of the upper, lower, and sidewalls of the housing has a specular interior surface, and the first and second ends of the housing can be adapted for being secured in place between spaced first and second duct sections.

Also as disclosed herein, the framework can comprise a first support structure disposed adjacent to the first end of the housing and a second support structure disposed adjacent to the second end of the housing. Each support structure comprises a peripheral frame and plural support legs that project inwardly from the peripheral frame to meet at a central retaining hub. The intake nose cone is supported by the central retaining hub of the first support structure, and the exhaust tail cone is supported by the central retaining hub of the second support structure. For instance, the intake nose cone and the exhaust tail cone can be supported by the central retaining hub of the first and second support structures respectively by support pins.

Also according to embodiments of the invention, the housing can have a plurality of walls, such as but not limited to upper, lower, and opposed sidewalls, and each wall can have a concave inwardly-facing surface. With that, ultra-violet light emitted by the ultra-violet light module can be focused within the housing to promote the purification of fluid, such as air, passing therethrough.

One will appreciate that the foregoing discussion broadly outlines certain important goals and features of the invention to enable a better understanding of the detailed description that follows and to instill a better appreciation of the inventors' contribution to the art. Before any particular embodiment or aspect thereof is explained in detail, it must be made clear that the following details of construction and illustrations of inventive concepts are mere examples of the many possible manifestations of the invention.

DETAILED DESCRIPTION OF PREFERRED EMBODIMENTS

The Aeolian fluid purification system disclosed herein is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

Embodiments of the Aeolian fluid purification system disclosed herein are indicated generally at 10 in FIGS. 1 through 11. There, the Aeolian fluid purification system 10 comprises a modular structure for purifying air flowing through a ducted system. Within the scope of the invention, the Aeolian fluid purification system 10 can be incorporated as a component of a newly-constructed heating, ventilation, and air conditioning (HVAC) system, or the Aeolian fluid purification system 10 can be retrofitted into a pre-existing HVAC system, such as by being applied in replacement of a section of ductwork. The Aeolian fluid purification system 10 can thus be disposed along a path of air flow between a first duct section 100 and a second duct section 102 as shown, for instance, in FIGS. 2, 4, and 5.

Figure 1:
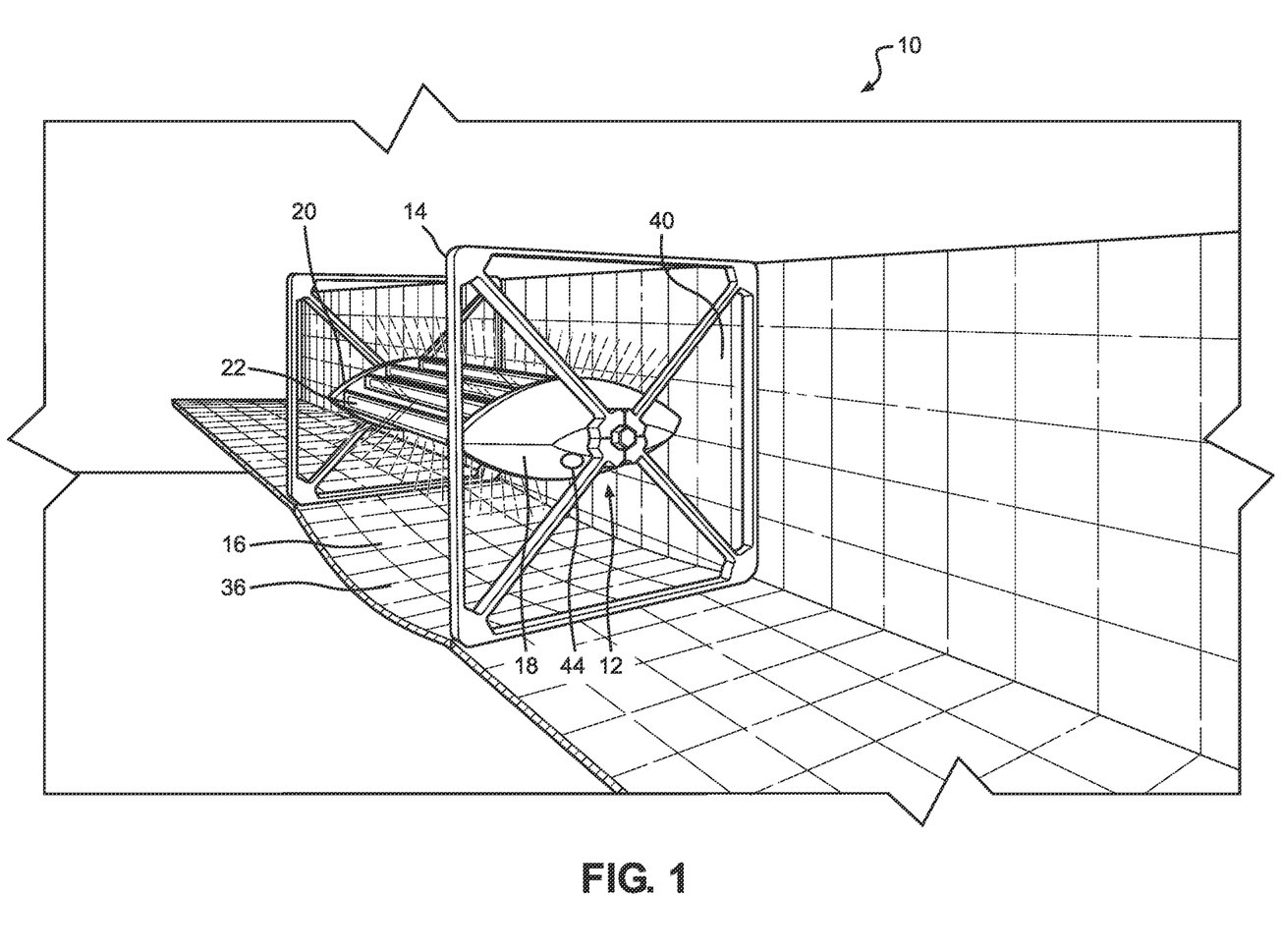
FIG. 1 is a partially-sectioned perspective view of an Aeolian fluid purification system according to the present invention interposed within a ducted system.
Figure 2:
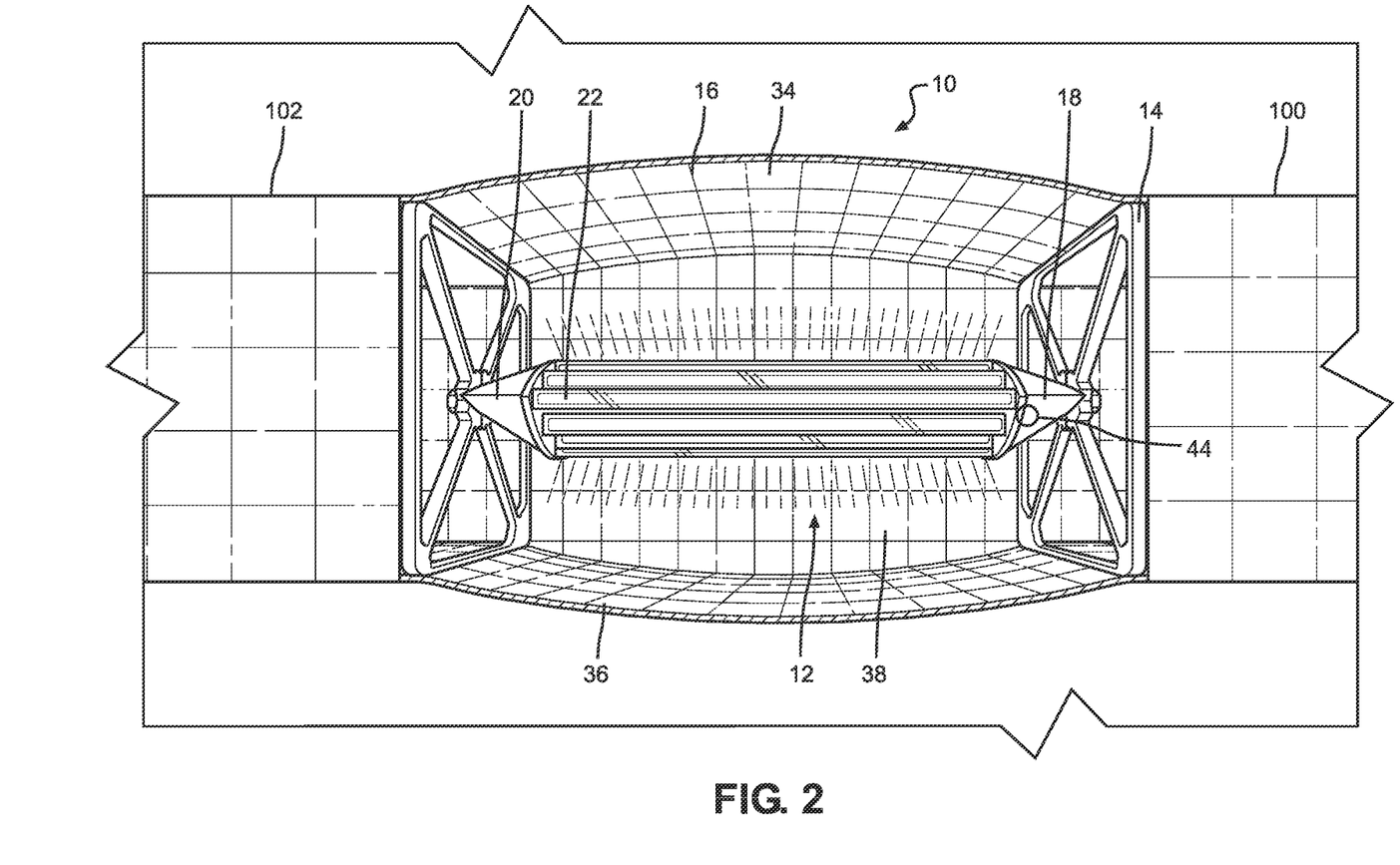
FIG. 2 is a partially-sectioned view in side elevation of the Aeolian fluid purification system again mounted within a ducted system.
Figure 3:
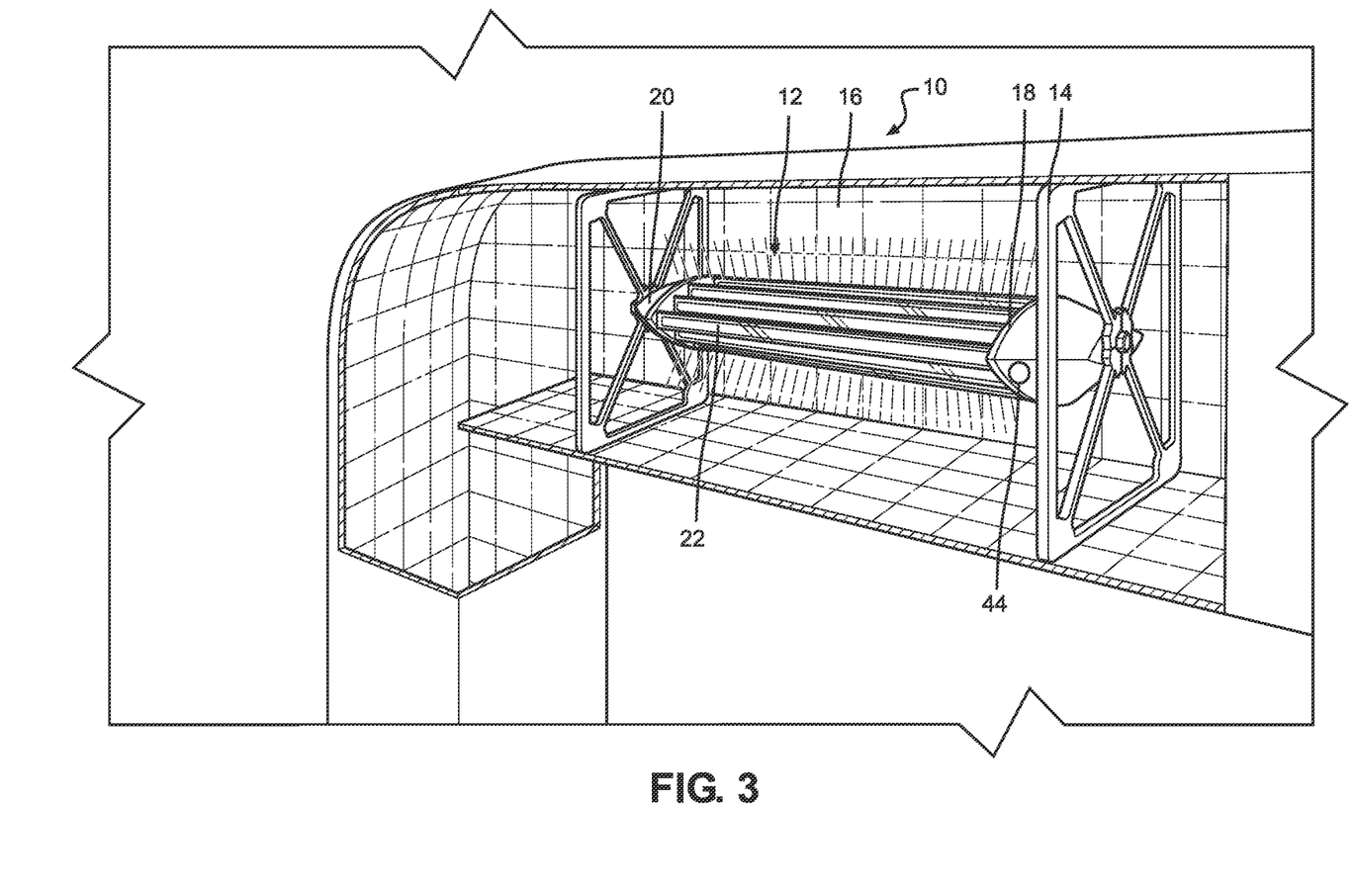
FIG. 3 is a partially-sectioned perspective view of the Aeolian fluid purification system mounted within a further ducted system.
Figure 4:
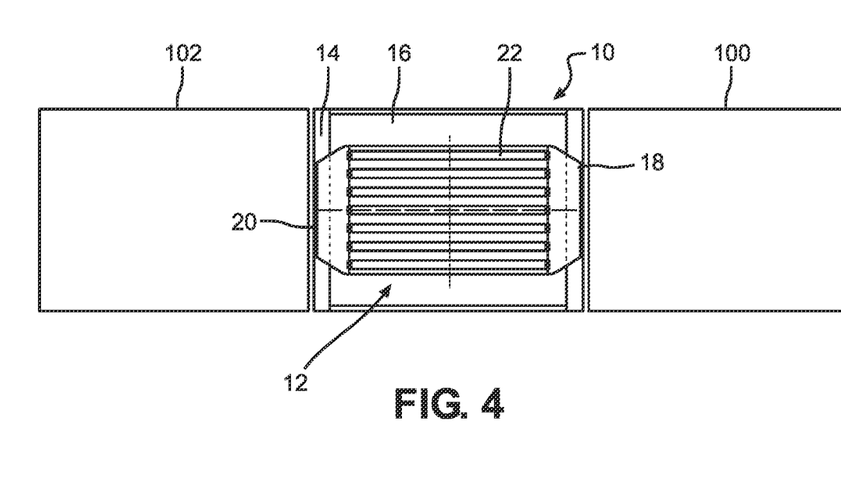
FIG. 4 is a top plan view of an embodiment of the Aeolian fluid purification system mounted within a ducted system.
Figure 5:
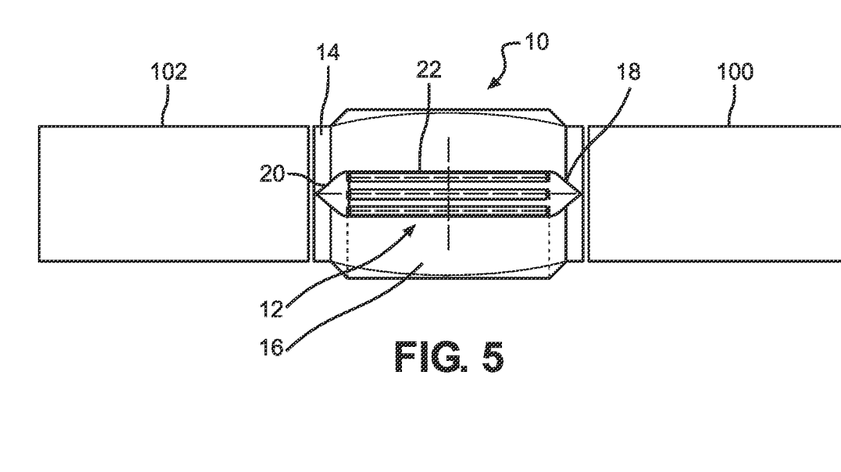
FIG. 5 is a view in side elevation of the Aeolian fluid purification system mounted within a ducted system.
Figure 6:
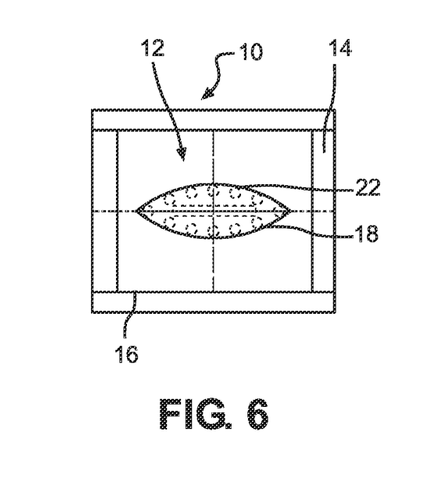
FIG. 6 is a view in front elevation of the Aeolian fluid purification system.
Figure 7:
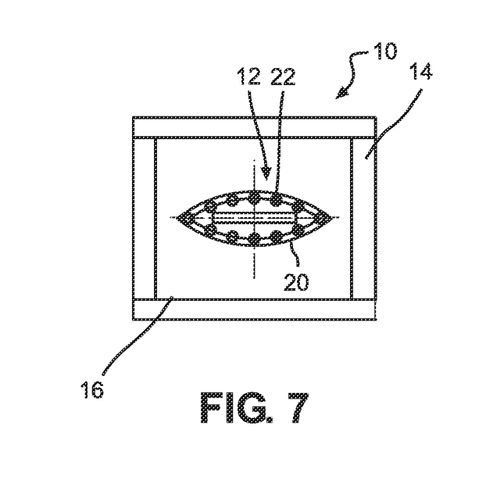
FIG. 7 is a cross-sectional view of the Aeolian fluid purification system.

As can be perceived by combined reference to FIGS. 1 through 3, for example, the Aeolian fluid purification system 10 can be considered to be founded on an ultra-violet light module 12. The light module 12 is concentrically retained by a framework 14 within a housing 16. The housing 16 is depicted here as being rectangular in cross section. The housing 16 thus has an upper wall 34, a lower wall 36, and opposed sidewalls 38 and 40. The walls 34, 36, 38, and 40 communicate longitudinally along the housing 16, and the light module 12 communicates in parallel thereto and longitudinally within the housing 16. The ends of the walls 34, 36, 38, and 40 are adapted for being secured in place between spaced first and second duct sections 100 and 102. Other configurations of the housing 16, such as round, elliptical, or otherwise-shaped constructions, are readily possible and within the scope of the invention except as it may be expressly limited by the claims.

Looking particularly to FIGS. 8 through 11, for instance, the framework 14 in the depicted embodiment comprises first and second support structures 24 and 26. Each support structure 24 and 26 is formed by a rectangular peripheral frame 28 that retains four support legs 30 that project inwardly from four respective corners of the peripheral frame 28 to meet at a central retaining hub 32. The first and second ends of the housing 16 and the system 10 are open except for the first and second support structures 24 and 26 supporting the light module 12.

The walls 34, 36, 28, and 40 of the housing 16 have highly specular interior surfaces that operate to reflect and re-reflect light emitted by the ultra-violet light module 12 within the housing 16. The reflective or specular interior surfaces can be created in any effective manner, including by surface finishing, by the application of a specular coating or material, or in some other manner. For instance, the specular interior surface could be created by the application of a reflective polyester film, by polishing, by glass mirror, or by any other method for creating a specular surface.

The ultra-violet light module 12 is configured to minimize disruption to the natural flow of air through the HVAC system. As such, the ultra-violet light module 12 has first and second aerodynamic end cones 18 and 20, which may alternatively be referred to as an intake nose cone 24 and an exhaust tail cone 26. The first and second end cones 18 and 20 cooperate to retain an array of tubular ultra-violet light bulbs 22. With respect to the light module 12, air traveling through the Aeolian fluid purification system 10 will pass from the first duct section 100 and into the system 10, initially passing through the end structure 24, then over the intake nose cone 24, then past the ultra-violet light bulbs 22, and then over the exhaust tail cone 26 before being exhausted through the end structure 26 to the second duct section 102.

The nose cone 18 and the tail cone 20 and the framework 14 could be constructed from any suitable material or materials. In certain embodiments, the first and second end cones 18 and 20 can, by way of example and not limitation, by constructed from fiberglass, from carbon fiber, from plastic, or from any other suitable material or combination of materials. Either or both end cones 18 and 20 could be coated, treated, and/or surface finished for still lower resistance to air flow. By way of example and not limitation, surface texturing may be incorporated to promote laminar flow and to reduce resistance. Additionally or alternatively, a low-friction coating, such as polytetrafluoroethylene (PTFE) or another material, or a pebbling, contouring, or other surface finish or application might be applied or formed to promote laminar flow still further.

Figure 8:
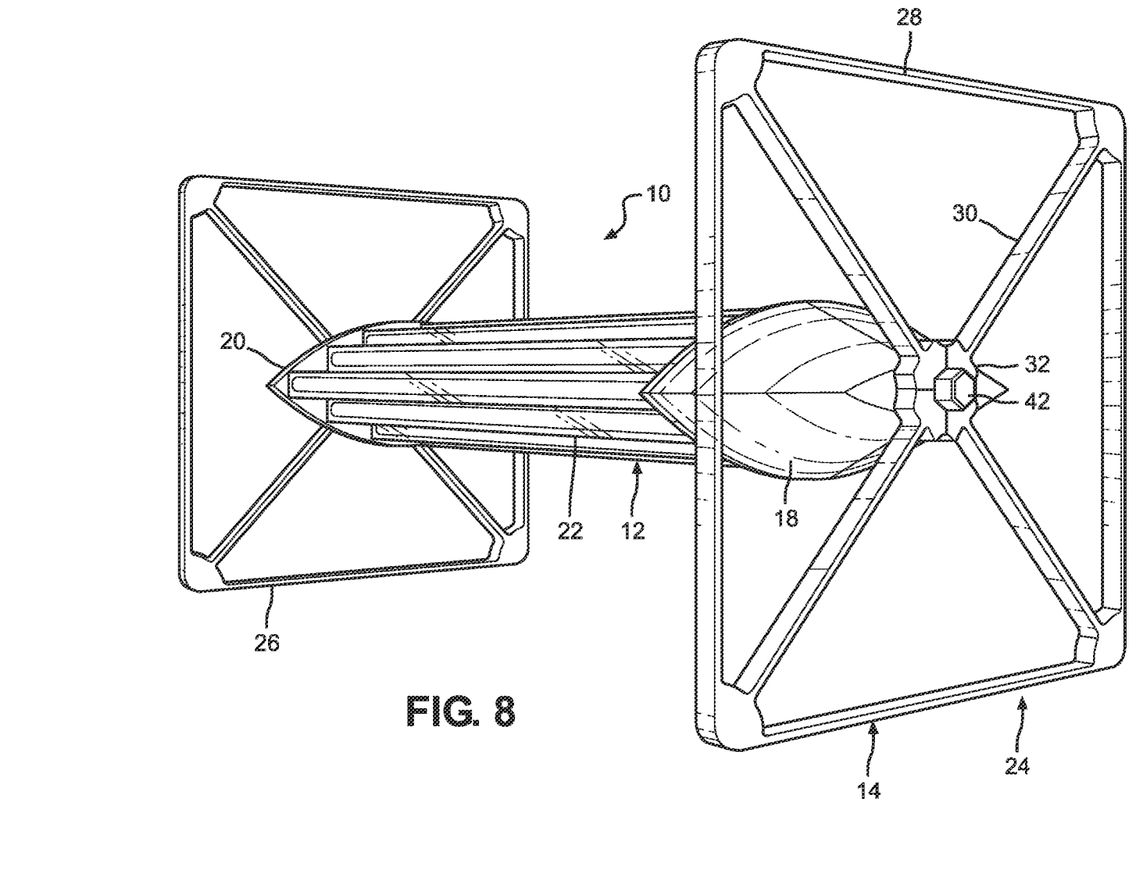
FIG. 8 is a perspective view of an embodiment of the Aeolian fluid purification system with the housing removed.
Figure 9:
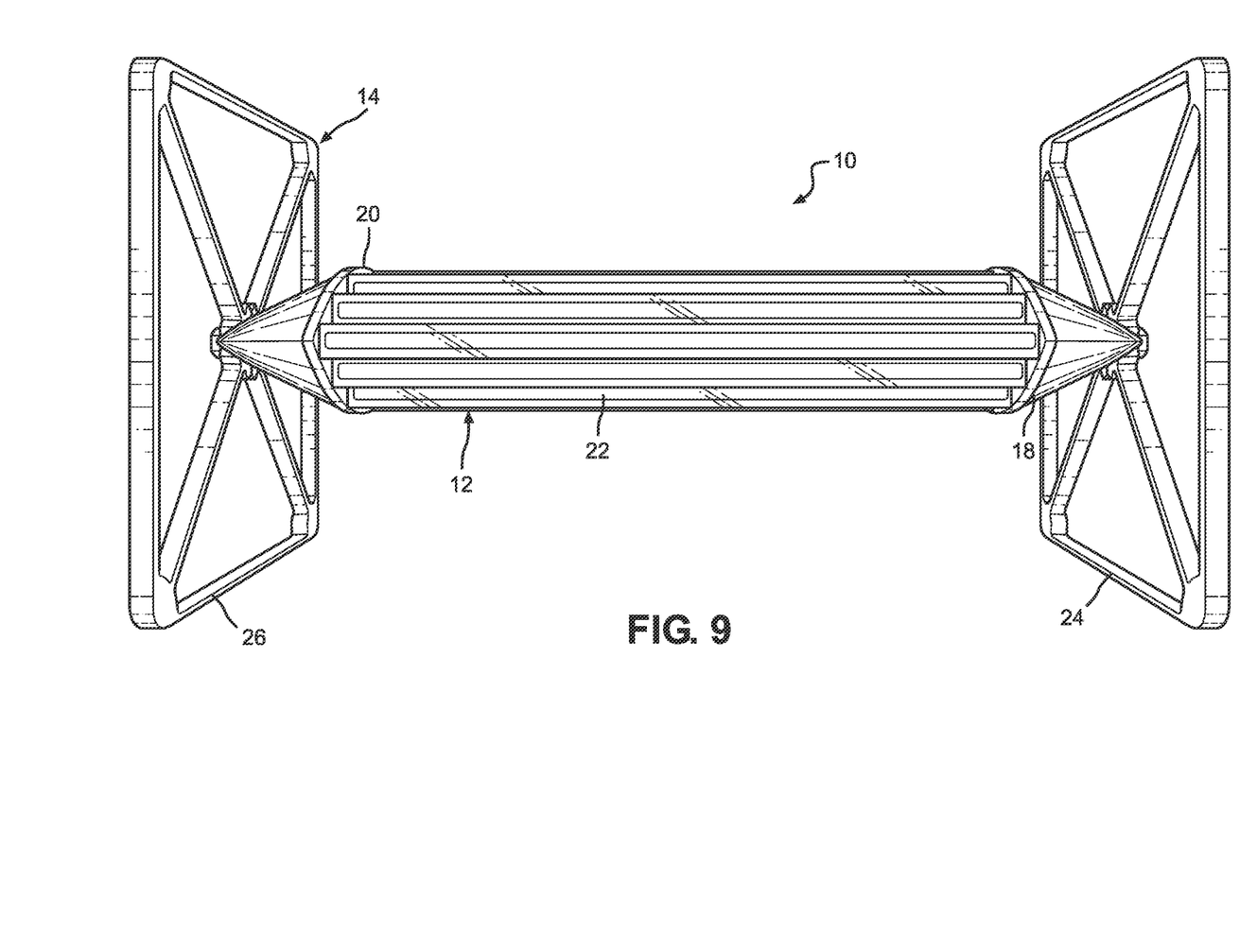
FIG. 9 is a lateral perspective view of the Aeolian fluid purification system with the housing removed.
Figure 10:
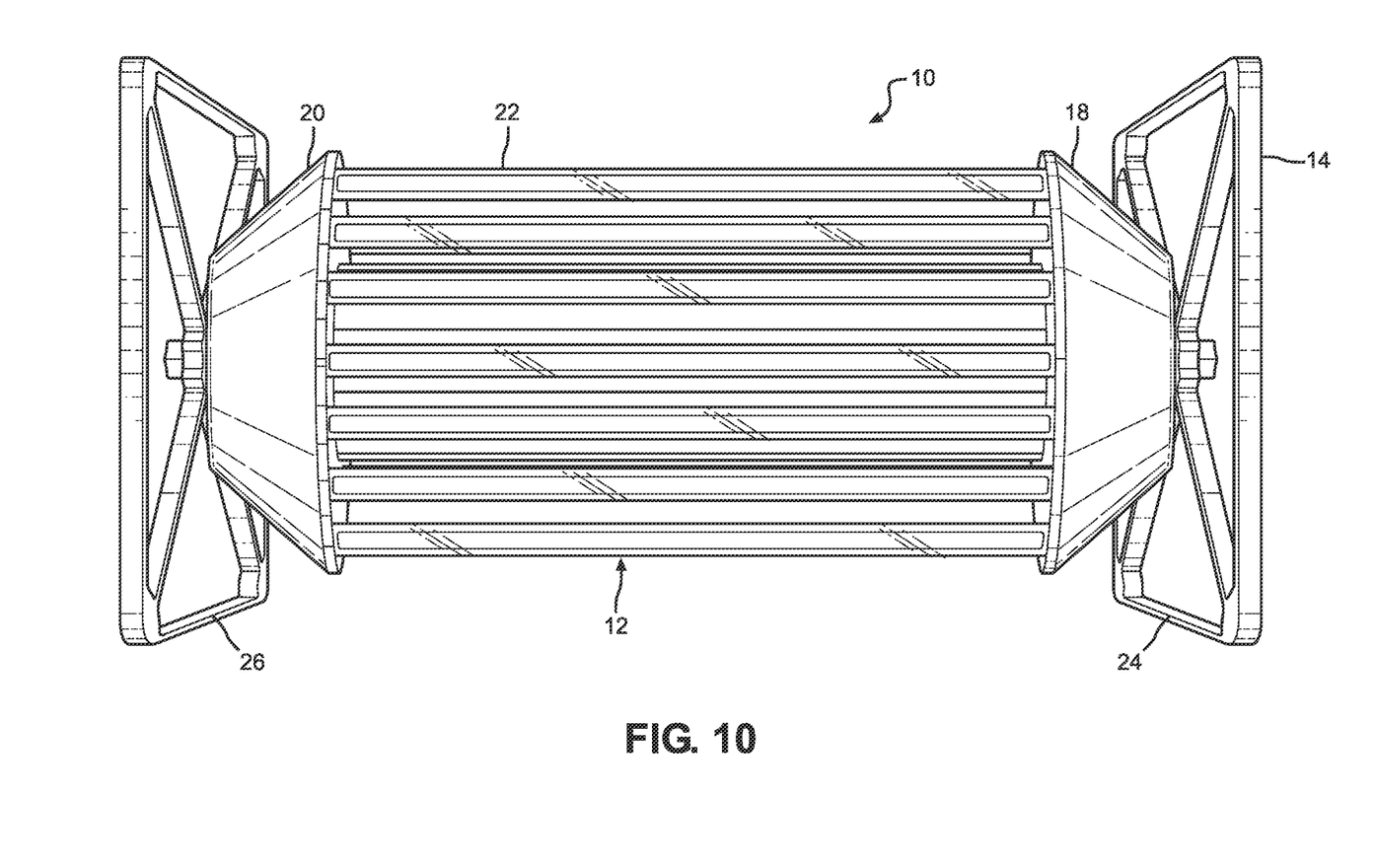
FIG. 10 is an upper perspective view of the Aeolian fluid purification system with the housing removed.
Figure 11:
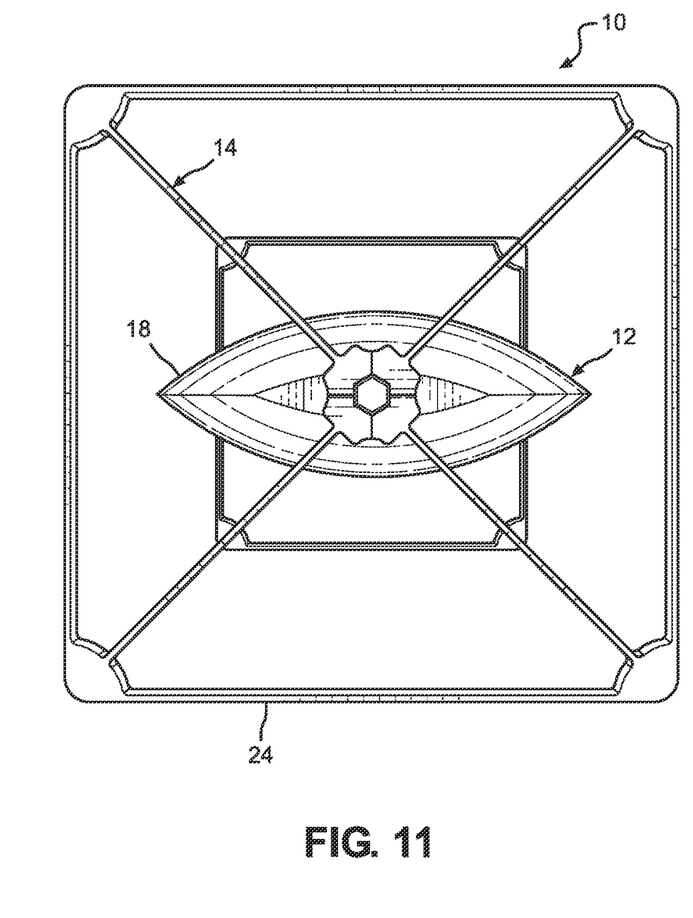
FIG. 11 is a frontal perspective view of the Aeolian fluid purification system.

In the present, non-limiting embodiment, the ultra-violet light module 12 has what can be characterized as a symmetrical aerofoil-shaped or eye-shaped lateral cross section. Each aerodynamic end cone 18 and 20 has a proximal portion bounded by upper and lower arcuate edges. The aerodynamic end cones 18 and 20 smoothly taper from the proximal portion to aerodynamic distal tip portions that in this embodiment are also eye-shaped in lateral cross section such that they are bounded by upper and lower arcuate edges. The distal tip portions of the end cones 18 and 20, and thus the light module 12 in general, are supported by the retaining hubs 32 of the end structures 24 and 26 respectively. For instance, as shown in FIG. 8, the end cones 18 and 20 are supported in the depicted embodiment by a support pin 42 that projects through the respective retaining hub 32 and into the respective end cone 18 or 20. With the open ends of the Aeolian fluid purification system 10, air passing through the HVAC system from the first duct section 100 to the second duct section 102 can flow over the ultra-violet light module 12 and through the Aeolian fluid purification system 10 with minimized impedance to flow.

The array of ultra-violet light bulbs 22 is retained by the proximal portions of the aerodynamic end cones 18 and 20 to span therebetween. The array of ultra-violet light bulbs 22 can be considered to have an upper array of bulbs 22 disposed along an upper arcuate path and a lower array of bulbs 22 disposed along a lower arcuate path. The upper and lower arrays of bulbs 22 share their terminal bulbs 22 as is shown perhaps most clearly in FIGS. 6 and 7. Like the proximal portions of the end cones 18 and 20, the upper and lower arrays of bulbs cooperate to be disposed along an eye shape. Ultra-violet light can thus be emitted by the array of ultra-violet bulbs 22 over a full 360-degree pattern surrounding the ultra-violet light module 12 through a module 12 that presents minimal disruption to laminar air flow. The specular surfaces surrounding the ultra-violet light module 12 defined by the upper, lower, and first and second sidewalls 34, 36, 38, and 40 operate to reflect and amplify the effects of the emitted ultra-violet light thereby maximize the effect of the Aeolian fluid purification system 10.

Electrical power is provided to the ultra-violet light module 12 and the fluid purification system 10 in general by any viable source of electrical power, including building power, battery power, generator power, or any other source of combination of sources. The ultra-violet light bulbs 22 and the ultra-violet light module 12 can be electrically powered and can be actuated in any appropriate manner. By way of example and not limitation, the ultra-violet light module 12 can be continuously powered, powered only during active fluid flow through the system 10, selectively powered by manual actuation, or automatically powered intermittently or in response to a detected pathogen. To that end, as FIGS. 1 through 3 show, the system 10 could further incorporate a detection subsystem 44 for detecting the presence of pathogens and triggering actuation of the ultra-violet light module 12 in response thereto.

Furthermore, as can be perceived by combined reference to FIGS. 1 through 6, the upper wall 34, the lower wall 36, and the sidewalls 38 and 40 in the depicted embodiment of the Aeolian fluid purification system 10 are bowed outwardly. Each wall 34, 36, 38, and 40 thus presents a concave inwardly-facing surface of highly-reflective material. As such, ultra-violet light emitted by the ultra-violet light module 12 tends to be reflected and focused toward a central portion of the Aeolian fluid purification system 10 in accordance with the invention's goal of achieving maximum fluid purification in combination with minimized disruption to air flow.

Air flowing through the ducted system from the first duct section 100 to the second duct section through the Aeolian fluid purification system 10 can thus be purified of pathogens, such as but not limited to virus pathogens, with minimized disruption and impedance to the flow of air through the ducted system. Newly-constructed HVAC systems can incorporate Aeolian fluid purification systems 10 as taught herein, and Aeolian fluid purification system 10 according to the invention can be readily applied to pre-existing HVAC systems to purify the air flowing therethrough and to enhance the safety of building occupants.

With certain details and embodiments of the present invention for an Aeolian fluid purification system 10 disclosed, it will be appreciated by one skilled in the art that numerous changes and additions could be made thereto without deviating from the spirit or scope of the present invention. This is particularly true when one bears in mind that the presented preferred embodiments merely exemplify the broader invention revealed herein. Accordingly, it will be clear that those with major features in mind could craft embodiments that incorporate those major features while not incorporating all of the features included in the preferred embodiments. Moreover, features, relationships, and dimensions shown in the drawings are intended merely to be illustrative and not limiting.

Therefore, the following claims shall define the scope of protection to be afforded to the invention. Those claims shall be deemed to include equivalent constructions insofar as they do not depart from the spirit and scope of the invention. It must be further noted that a plurality of the following claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

What is claimed as deserving of Letters Patent is:

1. A fluid purification system for purifying a fluid within a fluid flow system, the fluid purification system comprising:
   a housing with a first end open to fluid entering the housing, a second end open to fluid exhausted from the housing, and a specular interior surface;
   a framework fixed to the housing; and
   an aerodynamic ultra-violet light module retained by the framework within the housing and surrounded by the specular interior surface,
   wherein the ultra-violet light module has a first aerodynamic end cone comprising
   an intake nose cone disposed adjacent to the first end of the housing and
   a second aerodynamic end cone comprising
   an exhaust tail cone disposed adjacent to the second end of the housing,
   wherein the intake nose cone and the exhaust tail cone cooperate to retain a plurality of ultra-violet bulbs in an array to communicate longitudinally within the housing and
   wherein fluid entering the fluid purification system into the first end of the housing will pass over the intake nose cone prior to passing over the ultra-violet light bulbs and then over the exhaust tail cone before being exhausted through the second end of the housing,
   wherein the first and second aerodynamic end cones have tapered distal portions whereby the intake nose cone tapers toward the first end of the housing and whereby the exhaust tail cone tapers toward the second end of the housing,
   wherein the first and second aerodynamic end cones have proximal portions, and wherein the plurality of ultra-violet bulbs are retained by the proximal portions of the first and second aerodynamic end cones to freely span therebetween without any intervening structure between the plurality of ultra-violet bulbs.

2. The fluid purification system of claim 1, wherein the ultra-violet light module and the first and second aerodynamic end cones have symmetrical eye-shaped cross sections.

3. The fluid purification system of claim 2, wherein the array of ultra-violet light bulbs has an upper array of bulbs disposed along an upper arcuate path and a lower array of bulbs disposed along a lower arcuate path.

4. The fluid purification system of claim 1, wherein the specular interior surface comprises a reflective polyester film.

5. The fluid purification system of claim 1, wherein the housing is rectangular in lateral cross section with an upper wall, a lower wall, and opposed sidewalls and wherein each of the upper, lower, and sidewalls of the housing has a specular interior surface.

6. The fluid purification system of claim 5, wherein the first and second ends of the housing are adapted for being secured in place between spaced first and second duct sections.

7. The fluid purification system of claim 5, wherein the framework comprises a first support structure disposed adjacent to the first end of the housing and a second support structure disposed adjacent to the second end of the housing, wherein each support structure comprises a peripheral frame and plural support legs that project inwardly from the peripheral frame to meet at a central retaining hub, wherein the intake nose cone is supported by the central retaining hub of the first support structure, and wherein the exhaust tail cone is supported by the central retaining hub of the second support structure.

8. The fluid purification system of claim 7, wherein the intake nose cone is supported by the central retaining hub of the first support structure by a support pin and wherein the exhaust tail cone is supported by the central retaining hub of the second support structure by a support pin.

9. The fluid purification system of claim 1, wherein the housing has a plurality of walls and wherein each wall has a concave inwardly-facing surface.

10. The fluid purification system of claim 9, wherein the housing is rectangular in lateral cross section with an upper wall, a lower wall, and opposed sidewalls and wherein each of the upper, lower, and sidewalls of the housing has a specular interior surface.

11. A fluid purification system for purifying a fluid within a fluid flow system, the fluid purification system comprising:
    a housing with a first end open to fluid entering the housing, a second end open to fluid exhausted from the housing, and a specular interior surface;
    a framework fixed to the housing; and
    an aerodynamic ultra-violet light module retained by the framework within the housing and surrounded by the specular interior surface, wherein the ultra-violet light module has a first aerodynamic end cone comprising an intake nose cone disposed adjacent to the first end of the housing and a second aerodynamic end cone comprising an exhaust tail cone disposed adjacent to the second end of the housing, wherein the intake nose cone and the exhaust tail cone cooperate to retain a plurality of ultra-violet bulbs in an array to communicate longitudinally within the housing, wherein fluid entering the fluid purification system into the first end of the housing will pass over the intake nose cone prior to passing over the ultra-violet light bulbs and then over the exhaust tail cone before being exhausted through the second end of the housing, and wherein the first and second aerodynamic end cones have tapered distal portions whereby the intake nose cone tapers toward the first end of the housing and whereby the exhaust tail cone tapers toward the second end of the housing, wherein the first and second aerodynamic end cones have proximal portions, and wherein the plurality of ultra-violet bulbs are retained by the proximal portions of the first and second aerodynamic end cones to freely span therebetween without any intervening structure between the plurality of ultra-violet bulbs.

12. The fluid purification system of claim 11, wherein the ultra-violet light module and the first and second aerodynamic end cones have symmetrical eye-shaped cross sections.

13. The fluid purification system of claim 12, wherein the array of ultra-violet light bulbs has an upper array of bulbs disposed along an upper arcuate path and a lower array of bulbs disposed along a lower arcuate path.

14. The fluid purification system of claim 11, wherein the housing has a plurality of walls and wherein each wall has a concave inwardly-facing surface.

15. The fluid purification system of claim 14, wherein the housing is rectangular in lateral cross section with an upper wall, a lower wall, and opposed sidewalls and wherein each of the upper, lower, and sidewalls of the housing has a specular interior surface.

* * * * *